United States Patent [19]
Jackson

[11] Patent Number: 6,110,172
[45] Date of Patent: Aug. 29, 2000

[54] CLOSURE SYSTEM FOR OPEN ENDED OSTEOSYNTHESIS APPARATUS

[76] Inventor: Roger P. Jackson, 4706 W. 86th St., Prairie Village, Kans. 66207

[21] Appl. No.: 09/127,204

[22] Filed: Jul. 31, 1998

[51] Int. Cl.[7] .................................................. A61B 17/56
[52] U.S. Cl. ............................................................. 606/61
[58] Field of Search ................................ 606/61, 72, 73, 606/60, 69, 70, 71

[56] References Cited

U.S. PATENT DOCUMENTS

| | | | |
|---|---|---|---|
| 4,887,596 | 12/1989 | Sherman | 606/61 |
| 5,067,955 | 11/1991 | Cotrel . | |
| 5,346,493 | 9/1994 | Stahurski et al. . | |
| 5,496,321 | 3/1996 | Puno et al. | 606/59 |
| 5,562,663 | 10/1996 | Wisnewski et al. | 606/61 |
| 5,630,817 | 5/1997 | Rokegem et al. . | |

*Primary Examiner*—Michael Buiz
*Assistant Examiner*—(Jackie) Tan-Uyen T. Ho
*Attorney, Agent, or Firm*—John C. McMahon

[57] ABSTRACT

A closure system for an osteosynthesis apparatus includes an implant, such as a bone screw, a cap and a set screw which in combination is adapted for securement of a spinal rod or the like thereto. The implant includes a head having a rod receiving channel and tongue receiving grooves extending into opposed branches on opposite sides of the rod receiving channel. The cap includes a central portion with a set screw receiving bore extending therethrough and opposed tongues extending outward therefrom on opposite sides thereof. The cap is sized for insertion on the implant head such that the central portion extends through the U-shaped rod receiving channel and the tongues extend through the tongue receiving grooves. The cap includes a cylindrical rod receiving groove formed in a bottom thereof between the opposed tongues which is rounded upward at a front end thereof. Leading edges of the tongues are rounded downward and rearward to a flat bottom surface of the tongues. Front stops extend upward from the front of the tongues and rear stops extend upward from the rear of the tongues. The front and rear stops engage opposed faces of the implant head upon raising of the cap after insertion through downward advancement of the set screw through the set screw receiving bore and against a spinal rod.

20 Claims, 3 Drawing Sheets

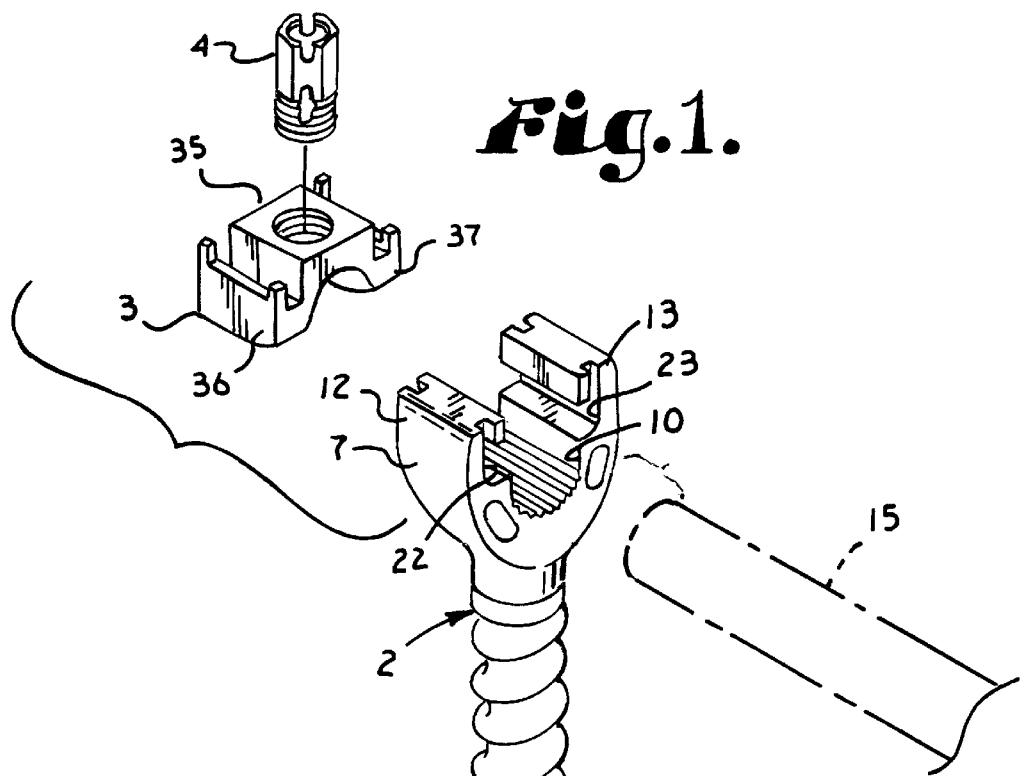
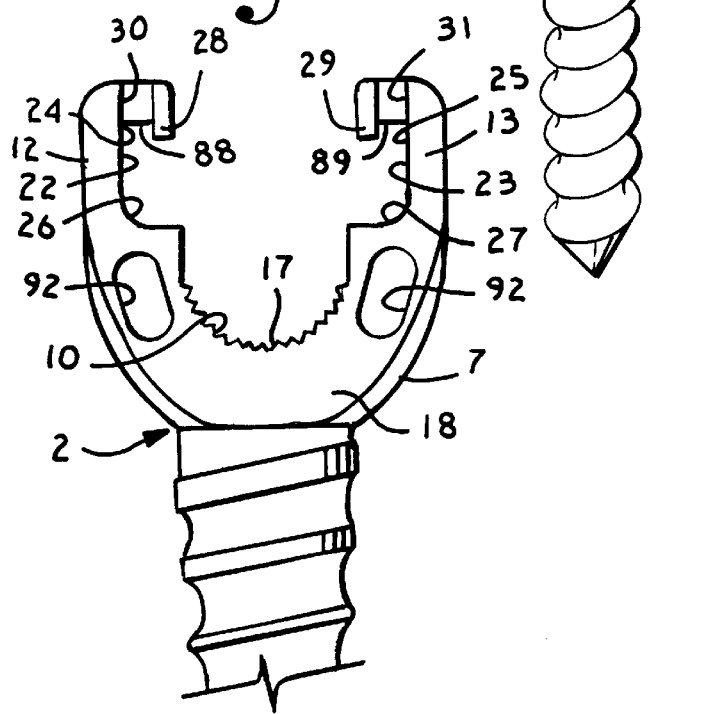
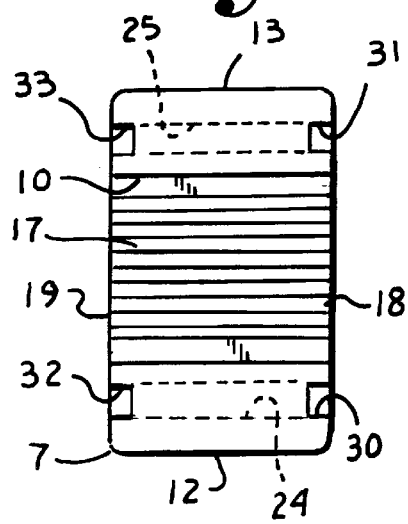

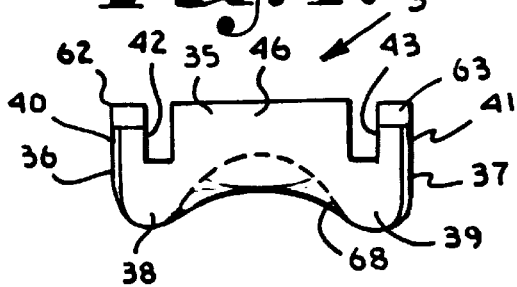
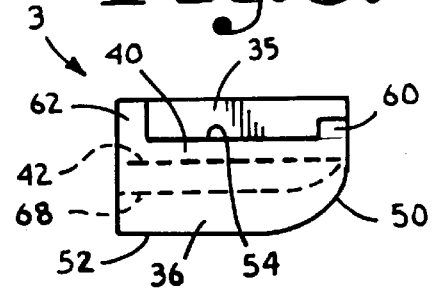
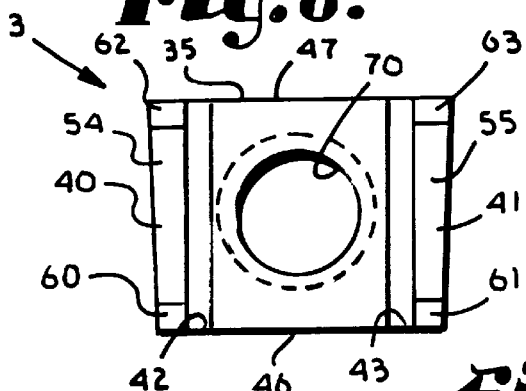
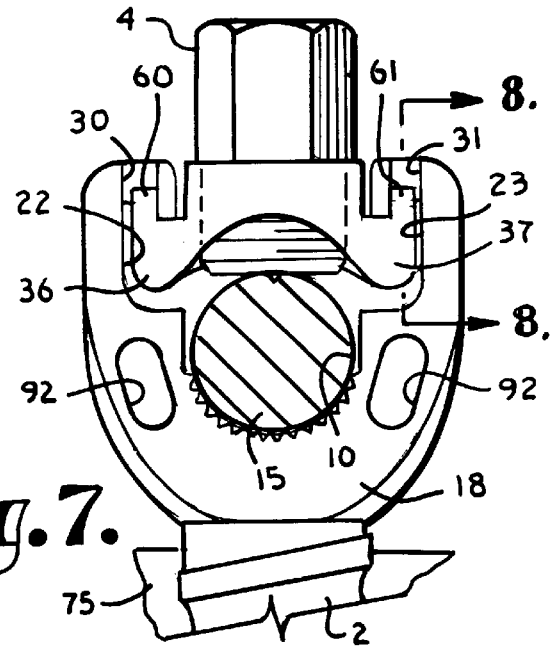
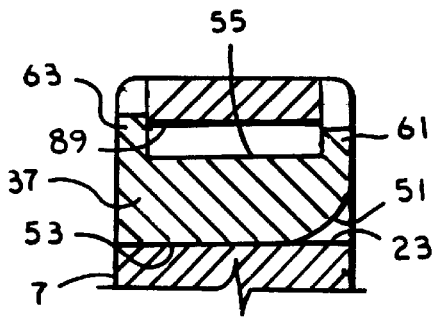
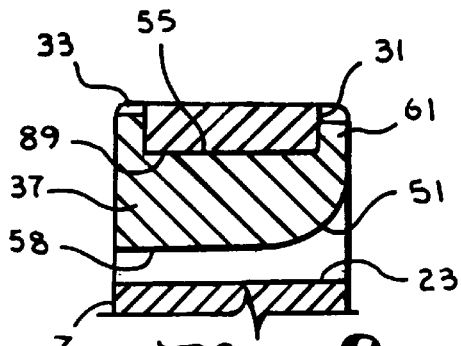

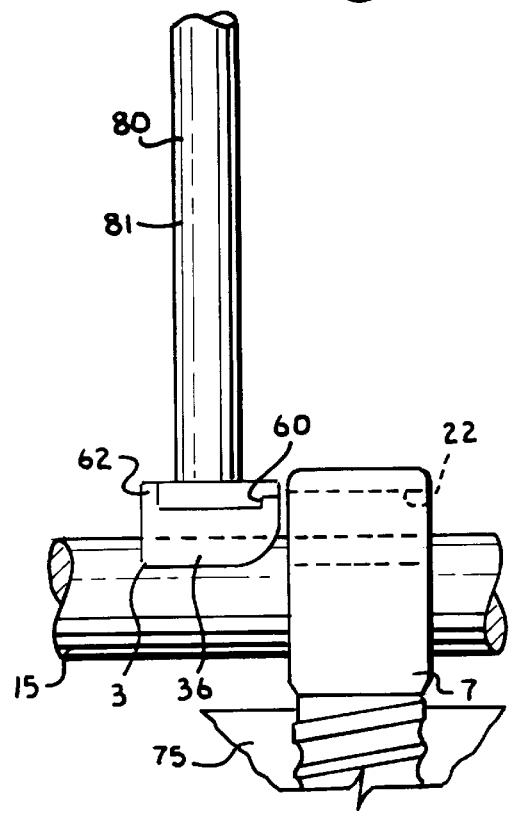
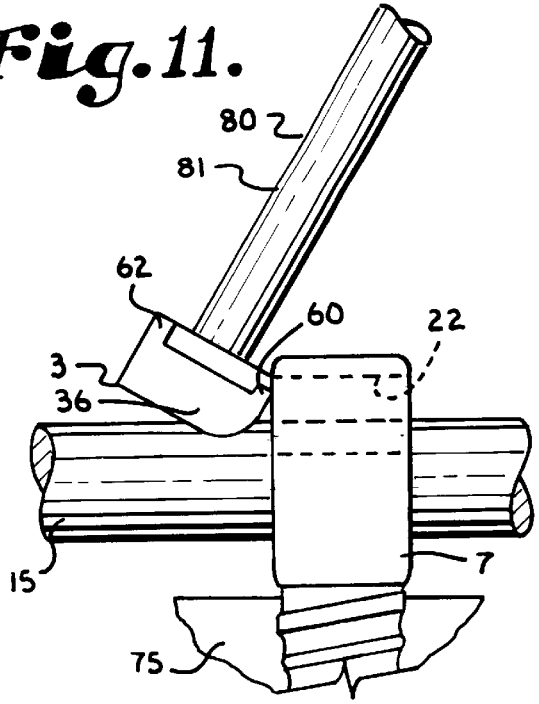
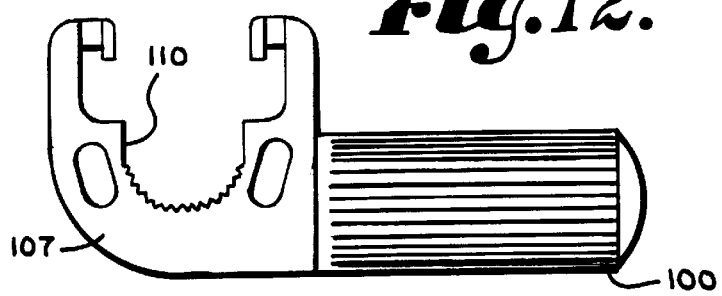

CLOSURE SYSTEM FOR OPEN ENDED OSTEOSYNTHESIS APPARATUS

BACKGROUND OF THE INVENTION

The present invention relates to improvements in closure systems for open ended osteosynthesis apparatus used to correct orthopedic deformities and, in particular, for use in spinal osteosynthesis.

Surgically implanted spinal osteosynthesis apparatus often include rods which are secured along at least a portion of the spine by a system of hooks, bone screws, including sacral screws and pedicle screws and transverse connectors for the purpose of stabilizing and adjusting spinal alignment.

The hooks, bones screws and transverse connectors or other spinal surgical implants may be of a closed end type or open end type. In a closed end type a bore, sized to receive a spinal rod, extends through the head of the implant. In an open end type the head of the hook, screw or connector generally incorporates a U-shaped groove sized to receive a spinal rod. A spinal rod is positioned in the U-shaped groove and a cap or other closure system is then secured to the head of the implant to enclose the spinal rod in the U-shaped groove.

In a relatively simple spinal osteosynthesis apparatus, open ended screws are screwed into the pedicle portion of the vertebra at desired locations and a spinal rod is then positioned in the U-shaped channel in each bone screw. A cap is then secured to the head of the screw to close off the U-shaped groove and to secure the spinal rod therein and a set screw extending through the cap is tightened against the rod to fix the translational and rotational relationship of the rod within the closed off U-shaped channel. The rods are bent or shaped, before or after insertion into the U-shaped channel, to maintain the spine in a desired configuration, to provide support to the spine and to exert desired corrective or stabilizing forces on the spine.

A slightly more complicated system uses transverse connectors in association with the bone screws to secure the spinal rods. The transverse connectors include an arm and a head. The head has a U-shaped channel formed therein. The arm of the connector is secured to the pedicle screw and the spinal rod is then inserted into the U-shaped channel of the transverse connector which is then capped off. A set screw secured within a threaded bore in the cap is then tightened to fix the relative position of the rod within the spinal rod bore.

One type of open end bone screw is shown in the Cotrel U.S. Pat. No. 5,005,562. The device in the Cotrel patent has threaded interior surfaces on the two upright branches that form the rod receiving channel therebetween and which receive a threaded set screw having a rod engaging point and outer ring. The set screw in Cotrel is tightened against the rod by advancing the set screw along the threads. However, this system has limitations. In particular, the ability of the set screw of Cotrel to grip and hold the rod is heavily dependent on the torque applied to the set screw during installation. Unfortunately, the torque is limited because too much torque will cause the branches to spread, thereby allowing the set screw to loosen and the implant to fail. Such failure can also occur when forces are applied to the implant during use, such as at time of muscular stress or during accidents when the back is jolted. To try to overcome this problem associated with the Cotrel device, the implant branches and set screw are increased in size to add strength and/or a retention ring is placed around the outside of the branches to reduce the likelihood of expansion. However, the strengthening adds substantial bulk to an implant and a ring adds bulk and complexity to the implant. In implants, it is important to try to reduce bulk rather than add to it, as it is desirable for the implants to be as low profile as possible.

In U.S. Pat. No. 5,562,663, I disclosed a cap for closing off a U-shaped channel of a bone screw with a rod inserted therein wherein the cap mates with the branches on opposite sides of the screw to prevent the branches from expanding radially outward. The cap incorporates a pair of curved tongues extending from the sides of a central portion which are adapted to be received in curved channels in opposed branches of the screw. The cap is rotated through an arcuate motion for insertion between the branches of the bone screw. Some practice is necessary for surgeons to familiarize themselves with the appropriate angel required to initiate insertion of the cap. Although use of the curved tongue and channel configuration can be advantageous in that the curved entry reduces the amount of open area behind the screw to permit insertion, the curved channels are relatively expensive to produce.

There remains a need for an improved closure system for an open ended spinal surgery implant which is relatively small and easy to install, which can be used to reliably fix the position of a spinal rod within the U-shaped channel of the implant and which is relatively inexpensive to manufacture.

SUMMARY OF THE INVENTION

The present invention comprises an osteosynthesis apparatus including an implant, such as a bone screw, a cap and a set screw adapted for securement of a spinal rod or the like thereto. The implant includes a head having an upwardly U-shaped rod receiving channel and tongue receiving grooves extending into opposed branches of the implant head on opposite sides of the rod receiving channel. The cap includes a central portion and opposed tongues extending outward from the central portion on opposite sides thereof. The cap is sized for insertion on the implant head such that the central portion extends through the U-shaped rod receiving channel and the tongues extend through the tongue receiving grooves. The cap includes a cylindrical rod receiving groove formed in a bottom thereof between the opposed tongues which is rounded upward at a front end thereof. The front surfaces or leading edges of the tongues are rounded downward and rearward to a bottom surface of the tongues which is generally flat. The rounded front edges of the cap and the upwardly curved rod receiving groove facilitate insertion of the cap through an arcuate motion or permit linear insertion of the cap. Front stops extend upward from the front of the tongues and rear stops extend upward from the rear of the tongues. The front stops are sized to permit the tongues to pass through the tongue receiving grooves while the rear stops are not. After the cap is inserted to the point the rear stops engage a face of the implant head, raising of the cap relative to the head manually or through advancement of a set screw extending though the cap central portion, advances the front stops into abutting relationship with an adjacent face of the implant head. Stop receiving grooves are formed in the opposed faces of the implant head and extend upwardly from the tongue receiving grooves and are adapted to receive the front and rear stops therein.

OBJECTS AND ADVANTAGES OF THE INVENTION

The objects and advantages of the invention include: to provide a closure system for securing spinal rods and the like in open ended implants which is easy to use; to provide such a system incorporating a cap interlockingly connectable to an open ended implant and fixedly securing a rod relative to the implant; to provide such a system in which the cap may be inserted on the implant from one side thereof parallel to an axis of the rod or arcuately relative thereto; to provide such a system in which the cap is slidingly secured to the open ended implant; to provide such a system in which the cap includes stops which upon complete insertion of the cap engage opposed faces of the cap and prevent the cap from sliding relative to the implant; and to provide such a system which is relatively inexpensive to manufacture.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

BRIEF DESCRIPTION OF THE DRAWINGS

FIG. 1 is an exploded perspective view of a closure system for open ended implants including an open ended bone screw, a cap and a set screw and showing, in phantom lines, a spinal rod to be secured in the head of the bone screw.

FIG. 2 is an enlarged and fragmentary front elevational view of the open ended bone screw.

FIG. 3 is an enlarged top plan view of the open ended bone screw.

FIG. 4 is an enlarged front elevational view of the cap.

FIG. 5 is an enlarged, left side elevational view of the cap.

FIG. 6 is an enlarged top plan view of the cap.

FIG. 7 is an enlarged and fragmentary front elevational view of the open ended bone screw showing the cap after it has been advanced to a fully inserted position and then raised through the advancement of the set screw through the cap and into engagement with a spinal rod.

FIG. 8 is a fragmentary cross-sectional view taken generally along line 8—8 of FIG. 7.

FIG. 9 is a view similar to FIG. 8 showing a portion of the cap positioned in a fully inserted alignment relative to the bone screw head and prior to upward advancement of the cap.

FIG. 10 is a fragmentary side view showing the cap just prior to securement to the bone screw and positioned against the spinal rod for sliding insertion along an axis parallel to the longitudinal axis of the spinal rod.

FIG. 11 is a fragmentary side view showing the cap just prior to securement to the bone screw and positioned for insertion along an arcuate path.

FIG. 12 is a front elevational view of the head of a transverse adapted to receive the cap and set screw for securing a rod thereto.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, and in particular FIG. 1, the reference numeral 1 refers to a bone screw assembly incorporating the closure system of the present invention. The bone screw assembly 1 includes a bone screw 2, a cap 3 and a set screw 4.

The bone screw 2 includes a head or body 7 and a lower threaded portion 8. As used herein, directional references are made with respect to the orientation of the screw 2 as shown in FIG. 2, with the head 7 being positioned at the top or upper end of the screw 2. A U-shaped channel 10 is formed in and extends into the head 7 from an upper end thereof so as to generally divide the head into first and second branches 12 and 13. The U-shaped channel 10 functions as a rod receiving channel adapted to receive a rod such as spinal rod 15.

A plurality of ridges 17 are formed in the head 7 adjacent a lower curved edge of the U-shaped channel 10. The ridges 17 extend from a first or front face 18 to a second or rear face 19 of the bone screw head 7 and are adapted to engage an outer surface of a spinal rod 15 positioned within the U-shaped channel 10 to provide frictional resistance to rotation of the spinal rod 15 about its longitudinal axis. The front and rear faces 18 and 19 of the screw head 7 are generally flat. As best seen in FIGS. 2 and 3 upper edges of the screw head 7 are generally rounded.

Tongue receiving slots 22 and 23 extend into the first and second branches 12 and 13 respectively of the screw head 7 from the inner surfaces thereof and from the front face 18 to the rear face 19. The tongue receiving slots 22 and 23 are both L-shaped including upper undercut sections 24 and 25 respectively and lower sidecut sections 26 and 27 respectively. The lower sidecut sections 26 and 27 generally extend perpendicular to upper undercut sections 24 and 25 and open into the U-shaped channel 10. The upper undercut sections 24 and 25 are separated from the U-shaped channel 10 by downwardly extending flanges or lips 28 and 29 respectively. Upper edges of the tongue receiving slots 22 and 23 are generally rectilinear.

Front stop receiving grooves 30 and 31 are formed in the front face 18 of the head 7 adjacent the upper undercut sections 24 and 25 respectively of the tongue receiving slots 22 and 23 respectively. The front stop receiving grooves 30 and 31 are the same width as the upper undercut sections 24 and 25 and extend from an upper edge of the upper undercut sections 24 and 25 to an upper end of the bone screw head 7. Rear stop receiving grooves 32 and 33 are formed in the rear face 19 of the head 7 adjacent the upper undercut sections 24 and 25 respectively of the tongue receiving slots 22 and 23 respectively. The rear stop receiving grooves 32 and 33 are the same width as the upper undercut sections 24 and 25 and extend from an upper edge of the upper undercut sections 24 and 25 to an upper end of the bone screw head 7.

Referring to FIGS. 4 through 9, the cap 3 includes a central portion 35 and side flanges or tongues 36 and 37 generally extending outwardly from opposite sides of the central portion 35. The tongues 36 and 37 are generally L-shaped, having foot portions 38 and 39 respectively connected to the central portion 35 and upwardly extending legs 40 and 41 respectively. The legs 40 and 41 are separated from the central portion 35 by lip receiving channels 42 and 43 respectively which extend from a front face 46 to a rear face 47 of the cap 3. Lower edges of the lip receiving channels 42 and 43 are generally flat, planar or rectilinear.

Leading edges 50 and 51 of tongues 36 and 37 respectively curve downward and rearward to flat bottom surfaces 52 and 53 thereof. Upper surfaces 54 and 55 of tongues 36 and 37 respectively are generally flat, planar or rectilinear except for front stops 60 and 61 which extend upward from upper surfaces 54 and 55 respectively at front ends thereof and rear stops 62 and 63 which extend upward from upper surfaces 54 and 55 respectively at rear ends thereof. Rear stops 62 and 63 generally extend upward and flush with an upper surface of the central portion 35. Front stops 60 and 61 are approximately half as tall as rear stops 62 and 63.

A downwardly opening rod receiving groove 68 is formed in the cap 3 along the bottom thereof generally between the tongues 36 and 37. The rod receiving groove 68 is curved slightly upward at a front end thereof such that the groove 68 is somewhat saddle shaped.

A set screw receiving bore 70 extends vertically and centrally through the central portion 35 of cap 3. The set screw receiving bore 70 is sized to receive set screw 4.

The cap 3 is sized for cooperative engagement with the bone screw head 7 as best seen in FIGS. 7 through 11. A cap 3 is secured to or installed in an open ended spinal surgical implant, such as bone screw 2 secured in vertebra 75, after a spinal rod 15 is positioned in U-shaped channel 10. The cap 3 may be installed on the screw head 7 using a sliding motion or a rotating motion. An elongated tool 80 having a stem 81 and a threaded tip 82 (not shown) threadingly secured within the set screw receiving bore 70 may be used to install the cap 3. To slide the cap 3 onto the screw head 7, the cap is generally positioned on top of the spinal rod 15 such that an upper portion of the rod 15 extends into the downwardly opening rod receiving groove 68 of cap 3 and the front face 46 of the cap 3 is positioned adjacent the rear face 19 of the screw head 7 such that the tongues 36 and 37 are generally aligned with the tongue receiving slots 22 and 23 respectively. The cap 3 is then slid in parallel alignment with a longitudinal axis of the rod 15 through the U-shaped channel 10 of the screw head 7 such that the tongues 36 and 37 slide through the tongue receiving slots 22 and 23 in the screw head 7. In particular, the upwardly extending legs 40 and 41 of cap 3 slide through the upper undercut sections 24 and 25 respectively and the foot portions 38 and 39 of cap 3 slide through the lower sidecut sections 26 and 27 respectively. Similarly, the lips 28 and 29 of the bone screw head 7 slide through the lip receiving channels 42 and 43 of cap 3 as the cap is inserted.

The height of the tongues 36 and 37 at the front stops 60 and 61 greater than the height of the associated tongue receiving slots 22 and 23. However, the height of the tongues 36 and 37 at the rear stops 62 and 63 is greater than the height of the associated tongue receiving slots 22 and 23. Therefore as the cap 3 is slid onto the bone screw head 7, the front stops 60 and 61 pass through the upper undercut sections 24 and 25 of the tongue receiving slots 22 and 23. Upper ends of the rear stops 62 and 63 abut against the rear face 19 of the bone screw head 7 within the rear stop receiving grooves 32 and 33 respectively, preventing the cap 3 from being slid further forward relative to the bone screw head 7. At this point of insertion with a lower portion of the cap 3 generally resting against spinal rod 15 the cap 3 may be classified as being in a fully inserted alignment.

The downwardly opening rod receiving groove 68 generally provides clearance for the upper portion of the spinal rod 15 as the cap 3 is inserted.

Once the cap 3 is inserted, the tool 80 may be removed and a set screw 4 is then threadingly inserted in the set screw receiving bore 70 in cap 3. The set screw 4 is then tightened down using a tool, not shown, until the set screw tip 85 engages the spinal rod 15, as shown in FIG. 7, so as to fix the rotational and translational orientation of the spinal rod 15 within the U-shaped channel 10 of bone screw head 7.

As the set screw 4 is threadingly advanced downward through the bore 70 in cap 3, the cap 3 initially advances upward relative to the bone screw head 7 until upper surfaces 54 and 55 of tongues 36 and 37, between front stops 60 and 61 and rear stops 62 and 63, engage undercut surfaces 88 and 89 of the screw head 7. In this alignment, the cap 3 may be classified as in a raised alignment. As the cap 3 is advanced upward, the front stops 60 and 61 advance into the front stop receiving grooves 30 and 31 respectively. Engagement of the front stops 60 and 61 against the front face 18 of the bone screw head 7 within the front stop receiving grooves 30 and 31 prevents the cap 3 from slipping rearward relative to the bone screw head 7 and provides further stability to the closure system. Similarly engagement of the flat upper surfaces 54 and 55 of tongues 36 and 37 against flat undercut surfaces 88 and 89 respectively of the screw head 7 provides for further stability of the closure system.

Although formed from a plurality of ridges 17, a lower periphery of the upwardly opening U-shaped rod receiving channel 10 is generally semi-cylindrical, conforming to the shape of rod 15 supported by the head 7 therein such that the rod 15 is supported by or abutted against the head 7 along the entire length of that portion of the rod extending through the rod receiving channel 10

As best seen in FIG. 6, the cap 3 is wedge shaped from front to back. In particular, the cap 3 is wider across the rear face 47 than the front face 46. The width of the cap 3 across the front face 46 is slightly smaller than the distance between outer edges of the first and second tongue receiving slots 22 and 23 and the width of the cap 3 across the rear face 47 is slightly greater than the distance between outer edges of the first and second tongue receiving slots 22 and 23. The branches 12 and 13 of the bone screw head 7 have sufficient give or flexibility to permit complete insertion of the wedge shaped cap 3 in the bone screw head 7. Wedging of the cap 3 into the head 7 provides further stability to the closure system.

As discussed briefly above and as best seen in FIG. 11, the cap 3 may also be inserted in the head 7 of bone screw 2 through a pivoting or rotating action. Such an approach to insertion may be necessary where space adjacent the bone screw head 7 is limited. The curvature of the curved leading edges 50 and 51 of tongues 36 and 37 respectively and the upwardly curved shape of the rod receiving groove 68 facilitate rotational insertion of the cap 3.

It is to be understood that the configuration of the front face 18 and rear face 19 of the bone screw head 7 are identical, and therefore the cap 3 may be inserted through the U-shaped channel 10 of bone screw head 7 from either the front face 18 or the rear face 19.

Referring to FIG. 2, a pair of ovate dimples 92 are formed in the front and rear faces 18 and 19 of bone screw head 7. The dimples are adapted to receive similarly shaped projections on specialized tools, not shown, adapted for use in installing the bone screw 2 in the vertebra 75 or for driving the spinal rod 15 into seated alignment within the U-shaped channel 10 of the head 7.

Forming the tongue receiving slots 22 and 23 with generally straight edges and surfaces from the front face 18 to the rear face 19 of the bone screw head 7 and not as curved slots greatly facilitates manufacturing in that the slots 22 and 23 may be broached or stamped into the head 7. Further use of straight slots 22 and 23 permits a wider variation in the angle or path of rotation through which the cap 3 may be inserted as opposed to a head incorporating curved tongue receiving slots, wherein the angle or arc of rotation through which the cap must be rotated for insertion is fairly limited to avoid binding of the tongues within the slots.

It is to be understood that although the set screw 4, shown for use with the closure system is of the type having a break-off head, a wide variety of set screws could be used with the closure system of the present invention. It is also to be understood that the set screw 4 could be preloaded in the set screw receiving bore 70 of cap 3 prior to insertion of cap 3 across the U-shaped channel 10 of bone screw head 7. In such an application tools designed for holding the cap 3 by engagement of the set screw 4 could be utilized for installation of the cap 3.

It is also to be understood that although the open ended implant shown in the drawings comprises a bone screw 2, the head configuration could be utilized with a wide variety of implants including hooks and transverse connectors for similar purposes. For example, FIG. 12 shows a transverse connector 100 having a head 107 configured the same as head 7 for bone screw 2 so as to be adapted for securement of cap 3 thereto for securement of a spinal rod or the like in an upwardly opening U-shaped channel 110 of the transverse connector head 107.

It is to be understood that while certain forms of the present invention have been illustrated and described herein, it is not to be limited to the specific forms or arrangement of parts described and shown.

What is claimed and desired to be secured by Letters Patent is as follows:

1. An osteosynthesis apparatus adapted to engage a rod; said apparatus comprising:
    a) an implant having a head with an upwardly opening rod receiving channel formed therein and sized to receive a rod; said rod receiving channel separating a first branch of said head from a second branch; first and second tongue receiving grooves formed in said first and second branches respectively and opening into said upwardly opening rod receiving channel; each of said tongue receiving grooves including a downwardly opening undercut portion separated from said rod receiving channel by an overhanging lip; said first and second tongue receiving grooves extending from a first face to a second face of said head; a lower surface of each of said lips and a lower surface of each of said branches above said undercut portion of said tongue receiving groove being rectilinear;
    b) a cap having a central portion with a set screw receiving bore extending vertically therethrough and first and second tongues extending outwardly from opposite sides of said central portion; each of said tongues comprising a foot portion extending outward from said central portion and an upwardly extending leg extending upward from said foot portion and spaced apart from said central portion by a lip receiving groove; an upper surface of each of said upwardly extending legs and an upper surface of each of said foot portions below said respective lip receiving groove being flat; said cap including at least one upward extending structure on an insertion leading side thereof; said cap adapted for securement to said implant head such that said central portion extends across said rod receiving channel and said first and second tongues extend through said first and second tongue receiving grooves such that said upwardly extending legs extend in said respective undercut portions of said tongue receiving grooves and said lips extend into said respective lip receiving groove; a front surface of each of said first and second tongues curving downward and rearward to a flat bottom portion of said respective tongue; said cap having a downwardly opening rod receiving groove formed in a lower surface thereof between said first and second tongues; said insertion leading side having a lower radiused surface that allows said cap to be tilted during insertion to allow said upward extending structure to clear elements of said branches during insertion; said radiused surface extending not more than half way across the bottom of said cap and a trailing side of said cap opposite said leading side being generally squared with the bottom of said cap.

2. The osteosynthesis apparatus as in claim 1 further comprising:
    a) first and second front stops extending upwardly from said first and second tongues respectively proximate a cap front face; said first and second tongues and said first and second front stops sized relative to said first and second tongue receiving grooves to permit said first and second tongues to slide through said first and second tongue receiving grooves to a fully inserted alignment; said first and second front stops advanceable into abutting relationship with said first face of said implant head through upward advancement of said cap from said fully inserted alignment.

3. An osteosynthesis apparatus adapted to engage a rod; said apparatus comprising:
    a) an implant having a head with an upwardly opening rod receiving channel formed therein and sized to receive a rod; said rod receiving channel separating a first branch of said head from a second branch; first and second tongue receiving grooves formed in said first and second branches respectively and opening into said upwardly opening rod receiving channel; each of said tongue receiving grooves including a downwardly opening undercut portion separated from said rod receiving channel by an overhanging lip; said first and second tongue receiving grooves extending from a first face to a second face of said head; a lower surface of each of said lips and a lower surface of each of said branches above said undercut portion of said tongue receiving groove being rectilinear;
    b) a cap having a central portion with a set screw receiving bore extending vertically therethrough and first and second tongues extending outwardly from opposite sides of said central portion; each of said tongues comprising a foot portion extending outward from said central portion and an upwardly extending leg extending upward from said foot portion and spaced apart from said central portion by a lip receiving groove; an upper surface of each of said upwardly extending legs and an upper surface of each of said foot portions below said respective lip receiving groove being flat; said cap adapted for securement to said implant head such that said central portion extends across said rod receiving channel and said first and second tongues extend through said first and second tongue receiving grooves such that said upwardly extending legs extend in said respective undercut portions of said tongue receiving grooves and said lips extend into said respective lip receiving groove; a front surface of each of said first and second tongues curving downward and rearward to a flat bottom portion of said respective tongue; said cap having a downwardly opening rod receiving groove formed in a lower surface thereof between said first and second tongues; a rear portion of said downwardly opening rod receiving groove being semi-cylindrical and curving upwards towards a front end thereof; and c) first and second front stops extending upwardly from said first and second tongues respectively proximate a cap front face; said first and second tongues and said first and second front stops sized relative to said first and second tongue receiving grooves to permit said first and second tongues to slide through said first and second tongue receiving grooves to a fully inserted alignment; said first and second front stops advanceable into abutting relationship with said first face of said implant head through upward advancement of said cap from said fully inserted alignment.

4. The osteosynthesis apparatus as in claim 3 wherein:

a) said cap is alternatively securable to said implant head through sliding advancement, from said first face to said second face, of said central portion through said rod receiving channel and said first and second tongues through said first and second tongue receiving grooves; such that said first and second front stops are alternatively advanceable into abutting relationship with said second face of said implant head through upward advancement of said cap from said fully inserted alignment.

5. The osteosynthesis apparatus as in claim 4 wherein:

a) first and second stop receiving grooves are formed in said first face of said implant head extending upward from said undercut portions of said first and second tongue receiving grooves and sized to receive said first and second front stops; and b) third and fourth stop receiving grooves are formed in said second face of said implant head extending upward from said undercut portions of said first and second tongue receiving grooves and sized to receive said first and second front stops.

6. The osteosynthesis apparatus as in claim 3 further comprising:

a) first and second rear stops extending upward from said first and second tongues respectively proximate a cap rear face; said first and second tongues and said first and second rear stops sized relative to said first and second tongue receiving grooves such that said first and second rear stops abut against said second face of said head as said cap is advanced to said fully inserted alignment.

7. The osteosynthesis apparatus as in claim 6 wherein:

a) said cap is alternatively securable to said implant head through sliding advancement, from said first face to said second face, of said central portion through said rod receiving channel and said first and second tongues through said first and second tongue receiving grooves; such that said first and second front stops are alternatively advanceable into abutting relationship with said second face of said implant head through upward advancement of said cap from said fully inserted alignment and said first and second rear stops alternatively abut against said first face of said implant head as said cap is advanced to said fully inserted alignment.

8. The osteosynthesis apparatus as in claim 7 wherein:

a) first and second stop receiving grooves are formed in said first face of said implant head extending upward from said first and second tongue receiving grooves and sized to receive said first and second front stops or said first and second rear stops; and b) third and fourth stop receiving grooves are formed in said second face of said implant head extending upward from said first and second tongue receiving grooves and sized to receive said first and second front stops or said first and second rear stops.

9. An osteosynthesis apparatus adapted to engage a rod; said apparatus comprising:

a) an implant having a head with an upwardly opening rod receiving channel formed therein sized to receive a rod; said rod receiving channel separating a first branch of said head from a second branch; first and second tongue receiving grooves formed in said first and second branches respectively, opening into said rod receiving channel, and extending from a first face to a second face of said head;

b) a cap having a central portion with a set screw receiving bore extending therethrough and first and second tongues extending outwardly from opposite sides of said central portion; said cap adapted for securement to said implant head through sliding advancement, from said second face to said first face, of said central portion through said rod receiving channel and said first and second tongues through said first and second tongue receiving grooves; said cap having first and second front stops extending upwardly from said first and second tongues respectively proximate a cap front face; said first and second tongues and said first and second front stops sized relative to said first and second tongue receiving grooves to permit said first and second tongues to slide through said first and second tongue receiving grooves to a fully inserted alignment; said first and second front stops advanceable into abutting relationship with said first face of said implant head through upward advancement of said cap from said fully inserted alignment.

10. The osteosynthesis apparatus as in claim 9 wherein:

a) leading edges of said first and second tongues curve downward and rearward to bottom surfaces thereof which are relatively flat.

11. The osteosynthesis apparatus as in claim 9 wherein:

a) said cap is alternatively securable to said implant head through sliding advancement, from said first face to said second face, of said central portion through said rod receiving channel and said first and second tongues through said first and second tongue receiving grooves; such that said first and second front stops are alternatively advanceable into abutting relationship with said second face of said implant head through upward advancement of said cap from said fully inserted alignment.

12. The osteosynthesis apparatus as in claim 11 wherein:

a) first and second stop receiving grooves are formed in said first face of said implant head extending upward from said first and second tongue receiving grooves and sized to receive said first and second front stops; and b) third and fourth stop receiving grooves are formed in said second face of said implant head extending upward from said first and second tongue receiving grooves and sized to receive said first and second front stops.

13. The osteosynthesis apparatus as in claim 9 further comprising:

a) first and second rear stops extending upward from said first and second tongues respectively proximate a cap rear face; said first and second tongues and said first and second rear stops sized relative to said first and second tongue receiving grooves such that said first and second rear stops abut against said second face of said head as said cap is advanced to said fully inserted alignment.

14. The osteosynthesis apparatus as in claim 13 wherein:

a) leading edges of said first and second tongues curve downward and rearward to bottom surfaces thereof which are relatively flat.

15. The osteosynthesis apparatus as in claim 13 wherein:

a) said cap is alternatively securable to said implant head through sliding advancement, from said first face to said second face, of said central portion through said rod receiving channel and said first and second tongues through said first and second tongue receiving grooves; such that said first and second front stops are alternatively advanceable into abutting relationship with said second face of said implant head through upward advancement of said cap from said fully inserted alignment and said first and second rear stops alternatively abut against said first face of said implant head as said cap is advanced to said fully inserted alignment.

16. The osteosynthesis apparatus as in claim 15 wherein:

a) first and second stop receiving grooves are formed in said first face of said implant head extending upward from said first and second tongue receiving grooves and sized to receive said first and second front stops or said first and second rear stops; and b) third and fourth stop receiving grooves are formed in said second face of said implant head extending upward from said first and second tongue receiving grooves and sized to receive said first and second front stops or said first and second rear stops.

17. An osteosynthesis apparatus adapted to cooperatively receive a rod to form an implanted medical support system; said apparatus comprising:

a) an implant having a head with a first and a second branch forming an open rod receiving channel therebetween; each of said branches having facing flanges with closure cap receivers on the underside thereof;

b) a closure cap having a body and at least one upwardly projecting structure near an insertion leading side of said cap and aligned with one of said branch flanges; said projecting structure being sized and shaped to mate with a receiving element of said branch;

c) said closure body having an insertion leading side that is curved and forms a frontward radiused surface with the bottom of said body that is sized and shaped to allow said projecting structure of said body in a tilted configuration, that is tiltable because of the curvature of the radiused surface, to pass beneath an associated branch flange; said radiused surface extending not more than approximately half way across the bottom of said body; a trailing side of said body opposite said leading side being non-radiused and generally squared with said cap bottom so as to strengthen said body.

18. The apparatus according to claim 17 wherein:

a) said radiused surface has a radius approximately equal to the width of said closure cap from top to bottom.

19. The apparatus according to claim 17 wherein:

a) said closure cap includes a lower central groove extending from front to rear and sized and shaped to be adapted to allow said cap to slide along a rod during installation.

20. The apparatus according to claim 17 wherein:

a) said upward projection includes front and rear stops on each side of said cap aligned with respective branch flanges that are sized and that are shaped to be received in mating receivers in said branches subsequent to assembly.

* * * * *